(12) United States Patent
Chang et al.

(10) Patent No.: US 10,621,722 B2
(45) Date of Patent: Apr. 14, 2020

(54) ITERATIVE ANALYZING METHOD FOR A MEDICAL IMAGE

(71) Applicant: Taichung Veterans General Hospital, Taichung (TW)

(72) Inventors: Chein-I Chang, Taichung (TW); Chi-Chang Clayton Chen, Taichung (TW); Jyh Wen Chai, Taichung (TW); Hsian-Min Chen, Taichung (TW)

(73) Assignee: TAICHUNG VETERANS GENERAL HOSPITAL, Taichung (TW)

( * ) Notice: Subject to any disclaimer, the term of this patent is extended or adjusted under 35 U.S.C. 154(b) by 125 days.

(21) Appl. No.: 16/031,375

(22) Filed: Jul. 10, 2018

(65) Prior Publication Data

US 2019/0096059 A1 Mar. 28, 2019

(30) Foreign Application Priority Data

Sep. 27, 2017 (TW) .............................. 106133240 A

(51) Int. Cl.
*A61B 6/00* (2006.01)
*G06T 7/00* (2017.01)
(Continued)

(52) U.S. Cl.
CPC .......... *G06T 7/0012* (2013.01); *A61B 6/5258* (2013.01); *G06T 7/11* (2017.01); *G06T 7/136* (2017.01); *G06T 7/62* (2017.01); *A61B 6/032* (2013.01); *A61B 6/5205* (2013.01); *A61B 6/5217* (2013.01); *G06T 2200/04* (2013.01); *G06T 2207/10081* (2013.01);
(Continued)

(58) Field of Classification Search
CPC ..... A61B 6/032; A61B 6/5205; A61B 6/5217; A61B 6/5258; G06T 2207/10081; G06T 2207/10088; G06T 2207/30016; G06T 2207/30096; G06T 2211/424; G06T 7/0012; G06T 7/11; G06T 7/136; G06T 7/62

See application file for complete search history.

(56) References Cited

U.S. PATENT DOCUMENTS 8,280,111 B2 * 10/2012 Kukshya .............. G06K 9/0063
382/103

* cited by examiner

*Primary Examiner* — Said M Elnoubi
(74) *Attorney, Agent, or Firm* — Muncy, Geissler, Olds & Lowe, P.C.

(57) ABSTRACT

The present invention disclosed an iterative analyzing method, which can detect the lesion in the image quickly. In brief, the iterative analysis method of the medical image disclosed by the present invention is roughly as follows: first, the original spectral image cube is expanded into a spectral image cube by a method of nonlinear dimensional-expansion, and then detecting the target's subpixel by the method of constrained energy minimization to produce an abundance image; the abundance image is fed back to the spectral image cube for create another spectral image cube by the nonlinear method. Furthermore, the abundance image is only used for detecting the subpixel of the target and does not include any spatial information, so, in order to obtain the spatial information of spectral image, it obtains the spatial information around the subpixel by using a blurring tool such as a Gaussian filter. After the spatial information is fed back to the spectral image cube, the subpixel target detection is repeatedly performed until a predetermined termination condition is satisfied.

10 Claims, 16 Drawing Sheets
(3 of 16 Drawing Sheet(s) Filed in Color)

(51) Int. Cl.
*G06T 7/11* (2017.01)
*G06T 7/62* (2017.01)
*G06T 7/136* (2017.01)
*A61B 6/03* (2006.01)

(52) U.S. Cl.
CPC ............... *G06T 2207/10088* (2013.01); *G06T 2207/30016* (2013.01); *G06T 2207/30096* (2013.01); *G06T 2211/424* (2013.01)

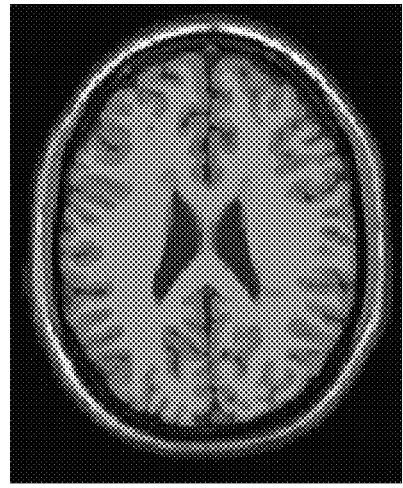
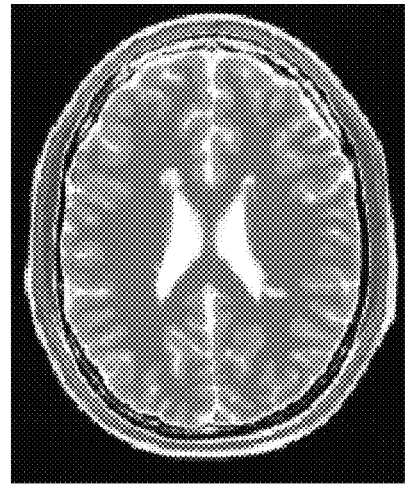
Fig. 4A                    Fig. 4B
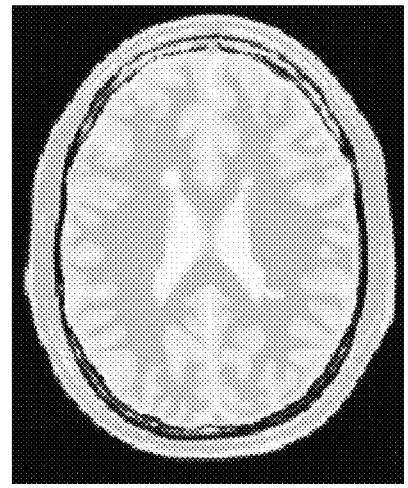
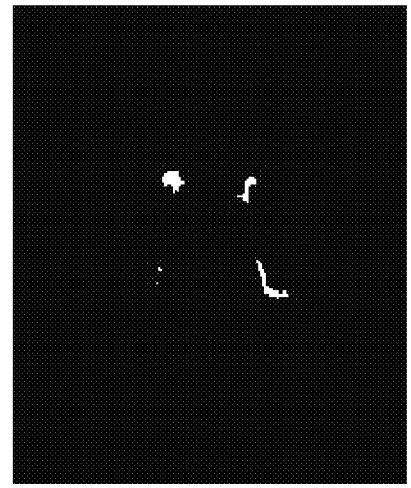
Fig. 4C                    Fig. 4D 1st iteration     2nd iteration     Lesions detection by Otsu's method 1st iteration     2nd iteration     Lesions detection by Otsu's method

T1　　　　　　　T2　　　　　　　PD

1st iteration　　　2nd iteration　　Lesions detection by Otsu's method

1st iteration     2nd iteration     Lesions detection by Otsu's method

T1     T2     PD

1st iteration    4th iteration    Lesions detection by Otsu's method

1st iteration    3rd iteration    Lesions detection by Otsu's method

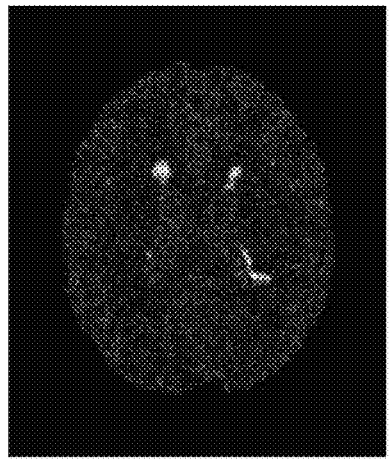 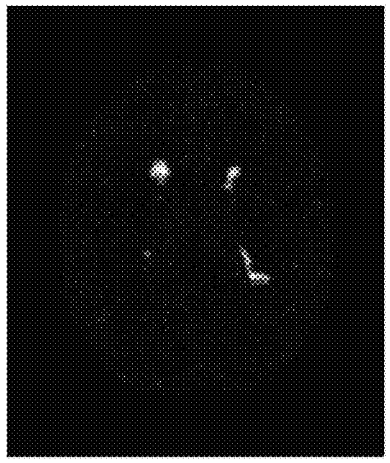 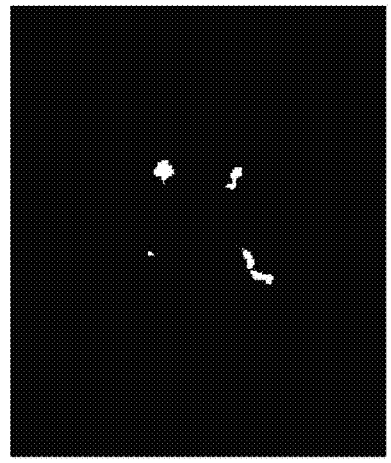
1st iteration     3rd iteration     Lesions detection by Otsu's method
Fig. 9C
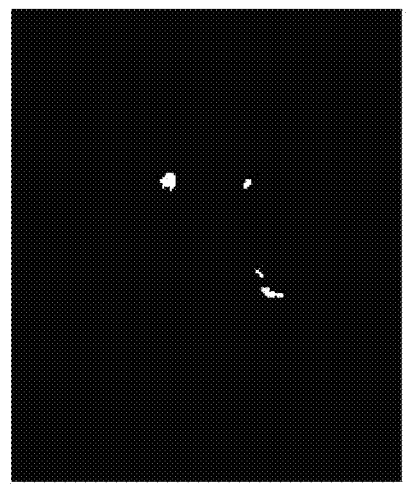
Lesions detection LST
Fig. 9D

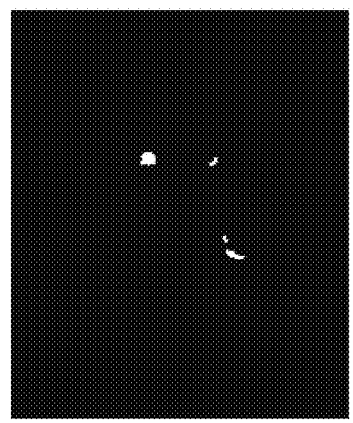
Fig. 10D
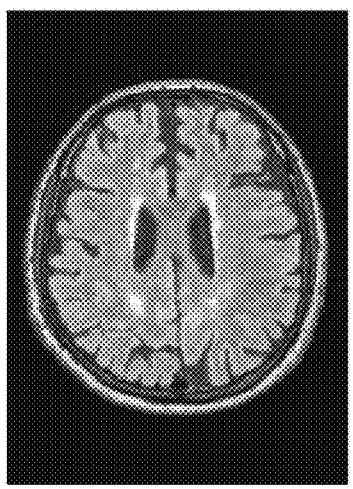 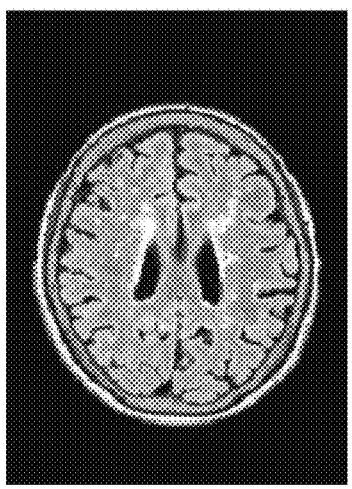 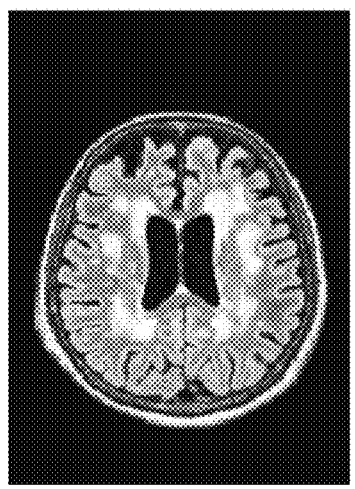
Fazekas grade 1     Fazekas grade 2     Fazekas grade 3
Fig. 11
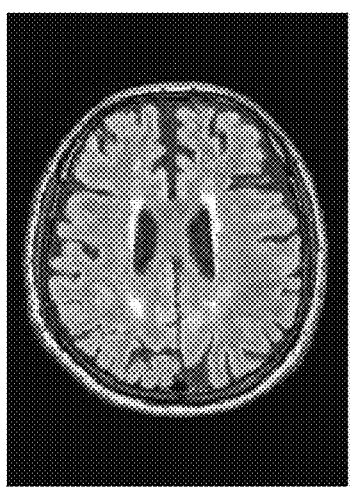 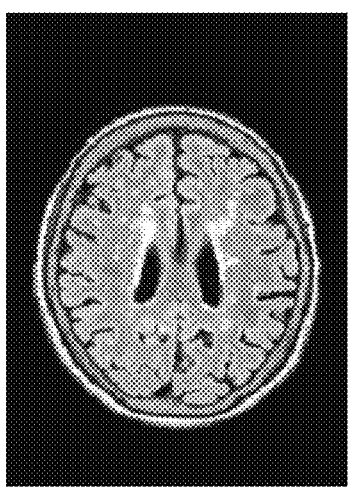 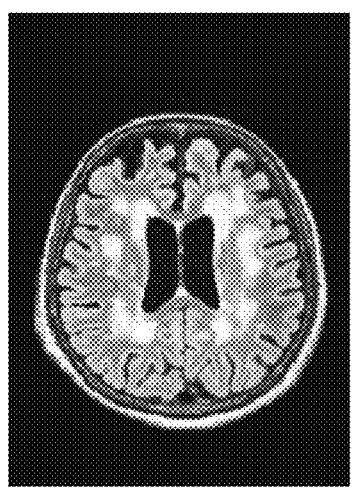
T1           T2           FLAIR
Fig. 12A

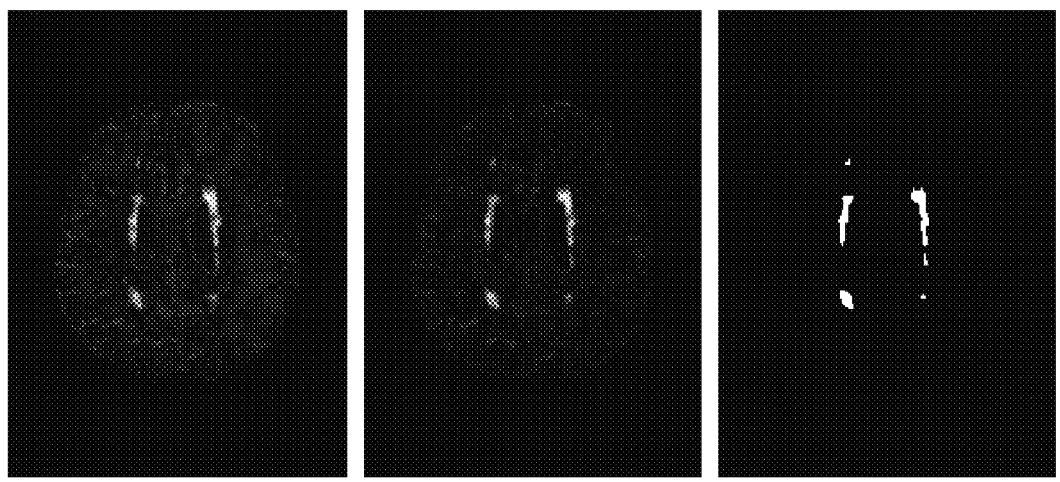
1st iteration     2nd iteration     Lesions detection by Otsu's method
Fig. 12B
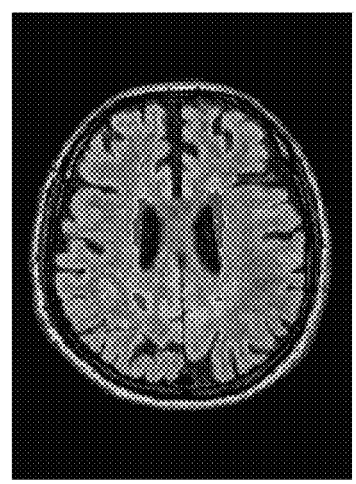 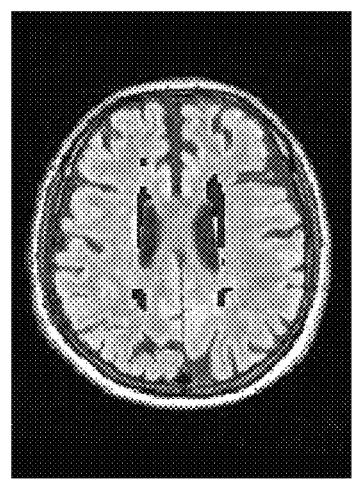
Fig. 12C       Fig. 12D
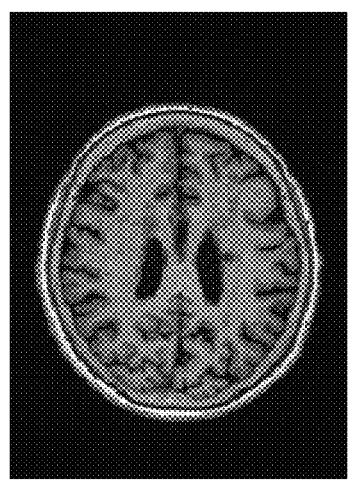  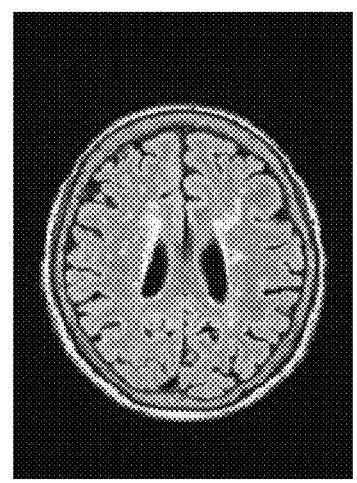
T1       T2       FLAIR
Fig. 13A

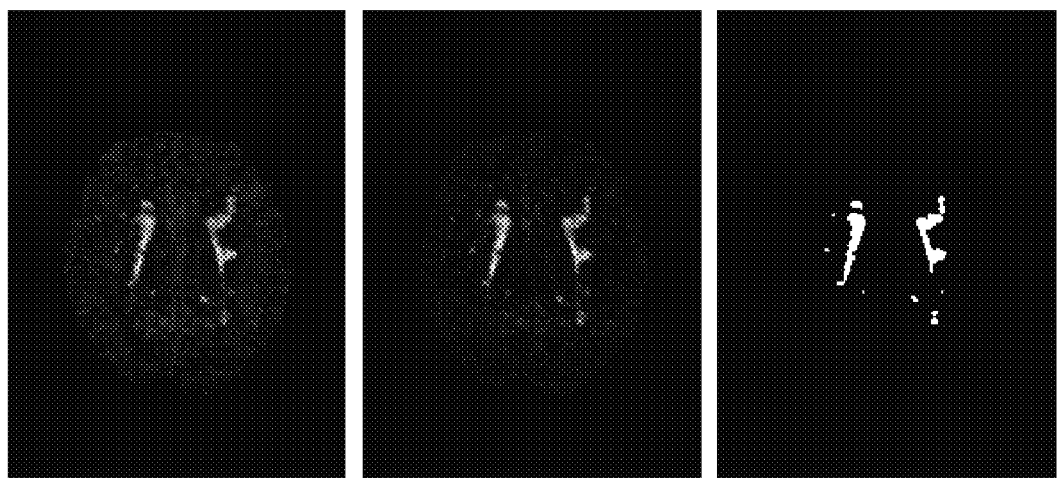
1st iteration     2nd iteration     Lesions detection by Otsu's method
Fig. 13B
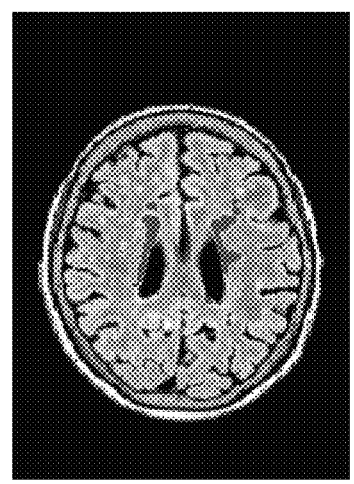 
Fig. 13C     Fig. 13D
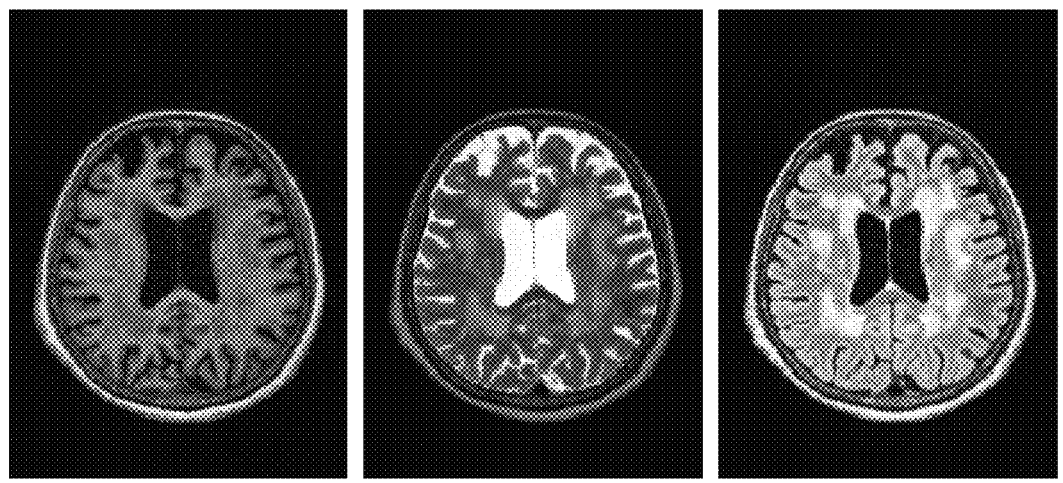
T1     T2     FLAIR
Fig. 14A 1st iteration     2nd iteration     Lesions detection by Otsu's method

ITERATIVE ANALYZING METHOD FOR A MEDICAL IMAGE

BACKGROUND

1. Field of the Invention

The present application is relative to an analyzing method for images, especially for an iterative analyzing method for a medical image.

2. Description of Related Art

White matter hyperintensities (WMH) are T2 or FLAIR sequences have been commonly observed on MR images of elderly people, and related to various geriatric disorders including cerebrovascular diseases, cardiovascular diseases, dementia, and psychiatric disorders. Therefore, many research pointed out that the white matter hyperintensities are the important indicator for detecting or diagnosing diseases, such as calculating the risk of stroke or dementia by the signal of white matter hyperintensities. However, at present, it analyzed the white matter hyperintensities of MRI (Magnetic resonance imaging) images by human visual evaluation and classification method which usually has to take a lot of time to complete. And it will increase the risk of analysis errors because of the manual operation and analysis.

The well-known hyperspectral subpixel target detection technique is called constrained energy minimization (CEM). CEM is a pixel-based technique and can detect the lesion of interest to produce an abundance image. But it has some defects as following when CEM is used for analyzing brain MRI images:

First, it is impossible to provide a threshold for determining the classification. In other words, it can not analyze the area of white matter hyperintensities in the image to classify correctly;

Second, CEM is a linear filter, so CEM can not be used to analyze a nonlinear image, that is, CEM can not analyze the area of white matter hyperintensities in the image.

Third, traditional hyperspectral influence processing method only uses pixels as the basis for analysis, but do not include the spatial information of the image itself, it will cause analyzing errors.

There is a need for a method of analyzing a medical image.

SUMMARY OF THE INVENTION

It is an object of the present invention to provide an iterative analyzing method for a medical image capable of preciously detecting the lesion by the mechanism of image feedback and images blurring to obtain the spatial information.

Another object of the present invention to provide an iterative analyzing method for a medical image is to providing the rule of termination condition for image feedback automatically, it can be more efficient to obtain the needed spatial information for analyzing images.

According to the present invention, the iterative analyzing method for a medical image, comprising the following steps:

(a) obtaining a $N^{th}$ spectral image cube, wherein N is a positive integer;

(b) detecting a relative matrix and a desired target subpixel from the $N^{th}$ spectral image cube to produce a $N^{th}$ abundance image;

(c) obtaining an absolute value of the $N^{th}$ abundance image for blurring and then producing a $N^{th}$ spatial spectral image;

(d) analyzing the $N^{th}$ spatial spectral image to produce a $N^{th}$ threshold and transferring the $N^{th}$ abundance image to a $N^{th}$ binary image by the $N^{th}$ threshold; and (e) calculating a $N^{th}$ similarity index by the $N^{th}$ threshold and the $N-1^{st}$ threshold, wherein:

the $N^{th}$ similarity index reaches a predetermined termination condition, the analyzing result includes the $N^{th}$ binary image and the $N^{th}$ spatial spectral image, or the $N^{th}$ similarity index does not reach the predetermined termination condition, it makes N of steps b to e to N+1 and collects the $N^{th}$ spectral image cube and the $N^{th}$ spatial spectral image to obtain a $N+1^{st}$ spectral image cube for repeating steps b to e.

In order to improve the defects of inadequate spectral dimensions and inseparable linearity in the prior art, in one embodiment of this present invention, when N is 1, the $N^{th}$ set of band images are dimensional-expanded from at least one original band image by a nonlinear method.

Furthermore, the original image is imaged by different wave signals. For example, the original image is MRI image, computed tomography image, or optical image.

In another embodiment of this present invention, it uses the method of constrained energy minimization to detect the image's abundance.

In order to obtain the spatial information of lesion, in the step c of one embodiment, it uses a smoothing filter to blur image, wherein the smoothing filter can be Gaussian filters, median filters, sort filters, or any tool to capture spatial information around the lesion. Moreover, if the noise of the detected image is higher, the mask size of the smoothing filter is bigger.

In embodiments of this present invention, the $N^{th}$ threshold is used for distinguishing the image foreground grayscale value from the image background grayscale value to show the lesion in the image.

In one embodiment of the present invention, the predetermined termination condition is the $N^{th}$ similarity index less than 0.7~0.9, such as 0.7, 0.75, 0.78, 0.8, 0.85, 0.88, 0.9. Preferably, the $N^{th}$ similarity index less than 0.8.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A shows MRI image containing multiple sclerosis (MS) lesions acquired by T1 with 0% noise and 0% INU (intensity non-uniformity).

FIG. 4B shows MRI image containing MS lesions acquired by T2 with 0% noise and 0% INU.

FIG. 4C shows MRI image containing MS lesions acquired by proton density (PD) with 0% noise and 0% INU.

FIG. 4D shows the ground truth of MRI image containing MS lesions.

FIG. 9C shows the lesion detection result of the original slice of MS MR brain images in FIG. 9A by the iterative analyzing method for a medical image of the present invention, using the Gaussian window size of 5×5 specified by σ=0.5.

FIG. 9D shows the lesion detection result of the original slice of MS MR brain images in FIG. 9A by the lesion segmentation tool.

FIG. 10D shows the lesion detection result of the original slice of MS MR brain images in FIG. 10A by the lesion segmentation tool.

FIG. 11 shows the three grades of Fazekas for lesion in the FLAIR images.

FIG. 12A shows the original MR images (T1, T2, FLAIR) with lesions of Fazekas grade 1.

FIG. 12B shows the lesion detection result of the original slice of MS MR brain images in FIG. 12A by the iterative analyzing method for a medical image of the present invention, using the Gaussian window size of 5×5 specified by σ=0.5.

FIG. 12C shows the lesion detection result of the original slice of MS MR brain images in FIG. 12A by the iterative analyzing method for a medical image of the present invention.

FIG. 12D shows the lesion detection result of the original slice of MS MR brain images in FIG. 12A by the lesion segmentation tool.

FIG. 13A shows the original MR images (T1, T2, FLAIR) with lesions of Fazekas grade 2.

FIG. 13B shows the lesion detection result of the original slice of MS MR brain images in FIG. 13A by the iterative analyzing method for a medical image of the present invention, using the Gaussian window size of 5×5 specified by σ=0.5.

FIG. 13C shows the lesion detection result of the original slice of MS MR brain images in FIG. 13A by the iterative analyzing method for a medical image of the present invention.

FIG. 13D shows the lesion detection result of the original slice of MS MR brain images in FIG. 13A by the lesion segmentation tool.

FIG. 14A shows the original MR images (T1, T2, FLAIR) with lesions of Fazekas grade 3.

DESCRIPTION OF THE PREFERRED EMBODIMENTS

Figure 1:
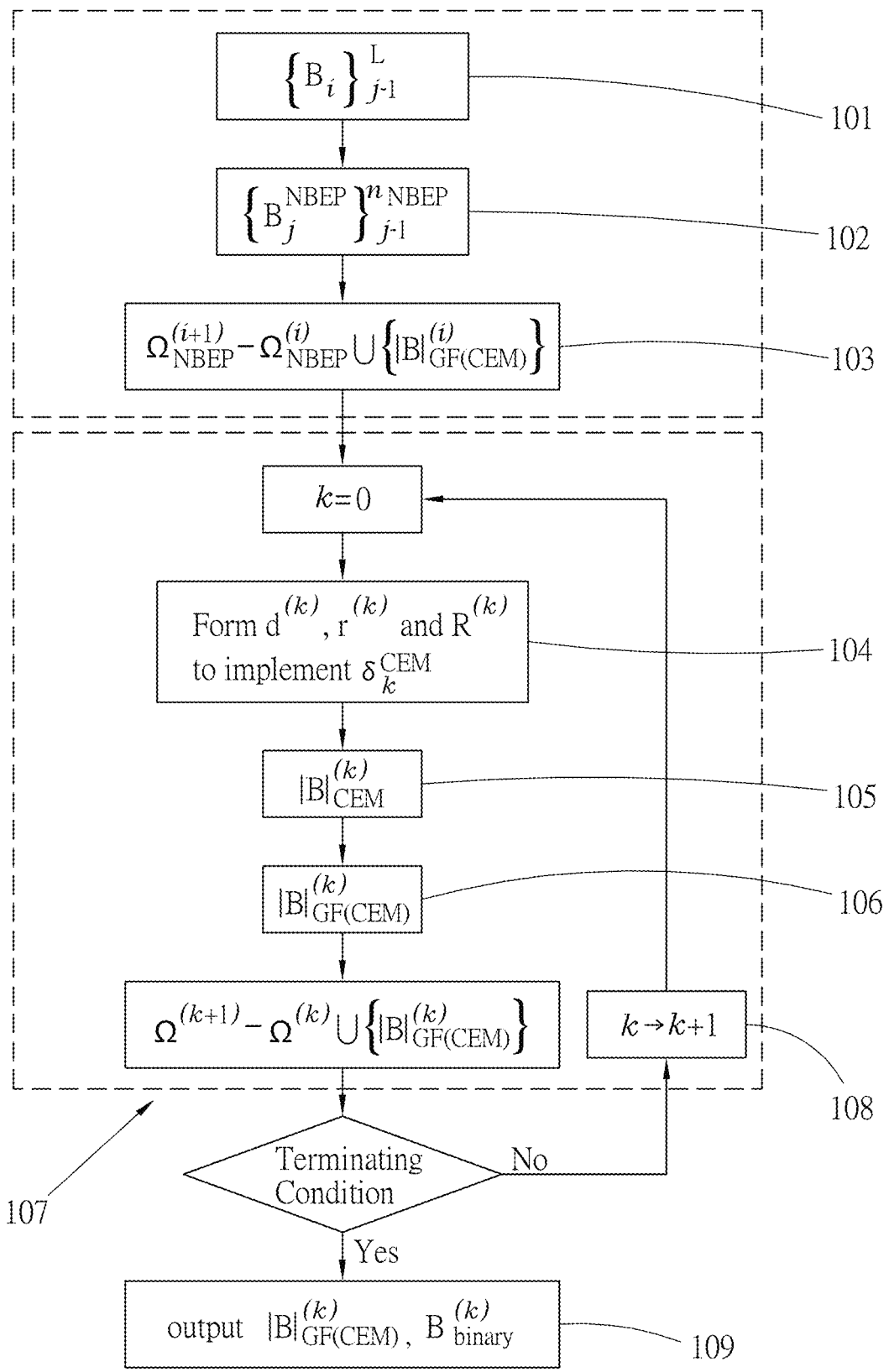
FIG. 1 is a flowchart in an embodiment of the present invention.

The present invention disclosed an iterative analyzing method, which can detect the lesion in the image quickly. In brief, the iterative analysis method of the medical image disclosed by the present invention is roughly as follows: first, the original spectral image cube is expanded into a spectral image cube by a method of nonlinear dimensional-expansion, and then detecting the target's subpixel by the method of constrained energy minimization to produce an abundance image; the abundance image is fed back to the spectral image cube for create another spectral image cube by the nonlinear method. Furthermore, the abundance image is only used for detecting the subpixel of the target and does not include any spatial information, so, in order to obtain the spatial information of spectral image, it obtains the spatial information around the subpixel by using a blurring tool such as a Gaussian filter. After the spatial information is fed back to the spectral image cube, the subpixel target detection is repeatedly performed until a predetermined termination condition is satisfied.

The method for nonlinear dimensional-expansion is as a nonlinear band dimensionality expansion (NBE). It collects the original hyperspectral image to produce a new spectral image by auto-correlation and cross-correlation.

For example, the nonlinear band dimensionality expansion is performed as follows:
Step 1. $1^{st}$-order band image: $\{B_l\}_{l=1}^{L}$=set of original band images.
Step 2. $2^{nd}$-order correlated band images:
 (i) $\{B_l^2\}_{l=1}^{L}$=set of auto-correlated band images;
 (ii) $\{B_k B_l\}_{k=1,l=1,k\neq l}^{L,L}$=set of cross-correlated band images.
Step 3. $3^{rd}$ order correlated band images:
 (i) $\{B_l^3\}_{l=1}^{L}$=set of auto-correlated band images;
 (ii) $\{B_k^2 B_l\}_{k=1,l=1,l\neq k}^{L,L}$=set of two cross-correlated band images;
 (ii) $\{B_k B_l B_m\}_{k=1,l=1,m=1,k\neq l\neq m}^{L,L,L}$=set of three cross-correlated band images.
Step 4. Other nonlinear correlated band images:
 (i) $\{\sqrt{B_l}\}_{l=1}^{L}$=set of band images stretched out by the square-root;
 (ii) $\{\log(B_l)\}_{l=1}^{L}$=set of band images stretched out by the logarithmic function.

In this embodiment of the present invention, it enhanced the brightness of the target area by constrained energy minimization to reach the aim of detecting the target area for lesion classification. Briefly, the basic principle of constrained energy minimization is to take a pixel value from a set of L-dimensional MR images. According to the coordinates of this pixel, it can obtain a set of L-dimensional vectors. From the set of L-dimensional vectors, a set of L-dimensional solutions can be obtained. The output value of inner product from the set of L-dimensional solutions and the coordinates of this pixel coordinate solutions is equal to 1 and try to suppress the value of inner product from other vectors and the coordinates of this pixel coordinate solutions. Therefore, if the vectors of the input coordinates are similar, the output value will be quite close to 1. To the grayscale image, if the set of solutions form the coordinate of lesion selected in the beginning can be regarded as a lesion filter, each pixel vector of the MR image is brought into operation in sequence to highlight the lesion and suppress the brightness of other normal tissues. Therefore, it can achieve the goal of lesion classification.

Specifically speaking, let L be the dimension of the spectral band, so the $i^{th}$ image vector is $r_i=(r_{i1}, r_{i2}, \ldots r_{iL})^T$, wherein $r_{ij}$ represents the $j^{th}$ pixel vector of the $j^{th}$ spectral band, $\{r_1, r_2, \ldots, r_N\}$ is the collection of all pixels of the MR image, and N is the total number of pixel in the image.

If the spectrum of the desired target is d and design a one-dimensional FIR linear filter for the desired target, assuming the pixel spectrum of the $i^{th}$ spectral image ($r_i$) passes through the one-dimensional FIR linear filter to output:

$$y_i = \sum_{l}^{L} w_l r_{il} = w^T r_i = r_i^T w \quad (1)$$

Calculating the result of average energy of total pixels $\{r_1, r_2, \Lambda, r_N\}$:

$$\frac{1}{N}\left[\sum_{i=1}^{N} y_i^2\right] = \frac{1}{N}\left[\sum_{i=1}^{N}(r_i^T w)^T r_i^T w\right] = w^T\left(\frac{1}{N}\left[\sum_{i=1}^{N} r_i r_i^T\right]\right)w = w^T R_{L\times L} w \quad (2)$$

Wherein $$R_{L\times L} = \frac{1}{N}\left[\sum_{i=1}^{N} r_i r_i^T\right]$$

can be seen as a form of matrix autocorrelation. So constrained energy minimization can solve the linear limit optimization problem as below.

$$\min \{w^T R_{L\times L} w\} \text{ should subject to } d^T w = 1 \quad (3)$$

The solution of formula (3) is $$w^* = \frac{R_{L\times L}^{-1} d}{d^T R_{L\times L}^{-1} d}.$$

According to above description, it shown that the filter of constrained energy minimization can detect $\delta_{CEM}(r)$, when the pixel vector (r) of the image is equal to d, $\delta_{CEM}(d)=1$ to subject to formula (3), wherein the value of $\delta_{CEM}(r)$ is obtained by the desired pixel (d) which is included in the image pixel (r).

Figure 2:
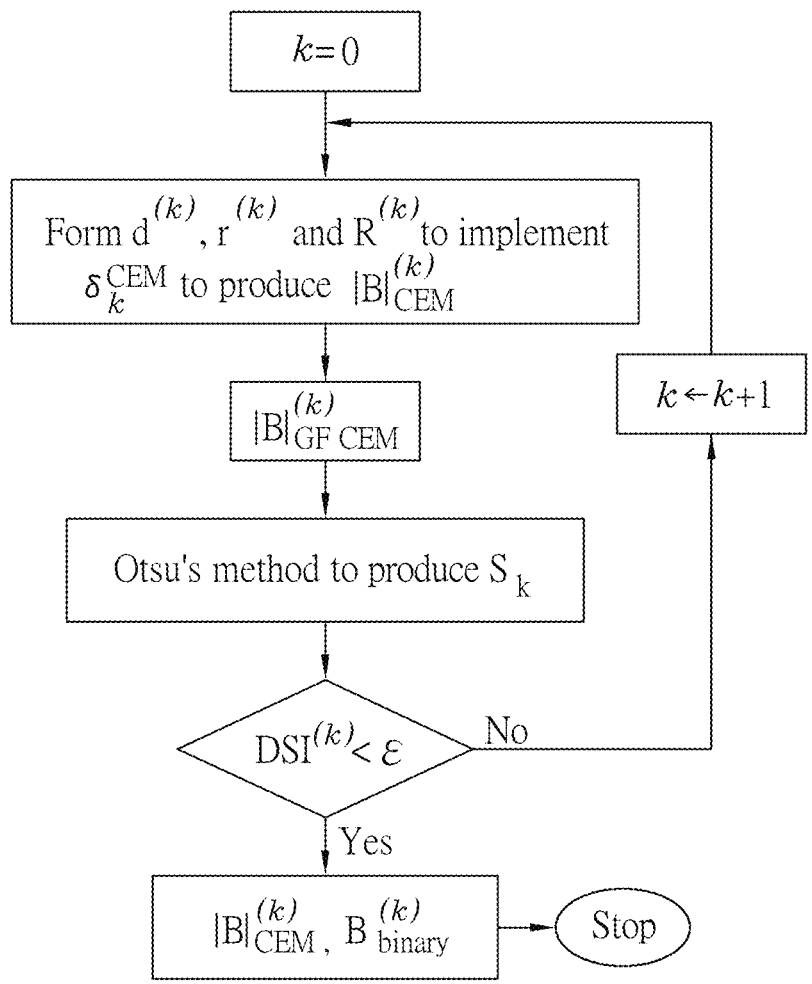
FIG. 2 shows a flowchart for deciding the terminating condition in the embodiment of the present invention.
Figure 3:
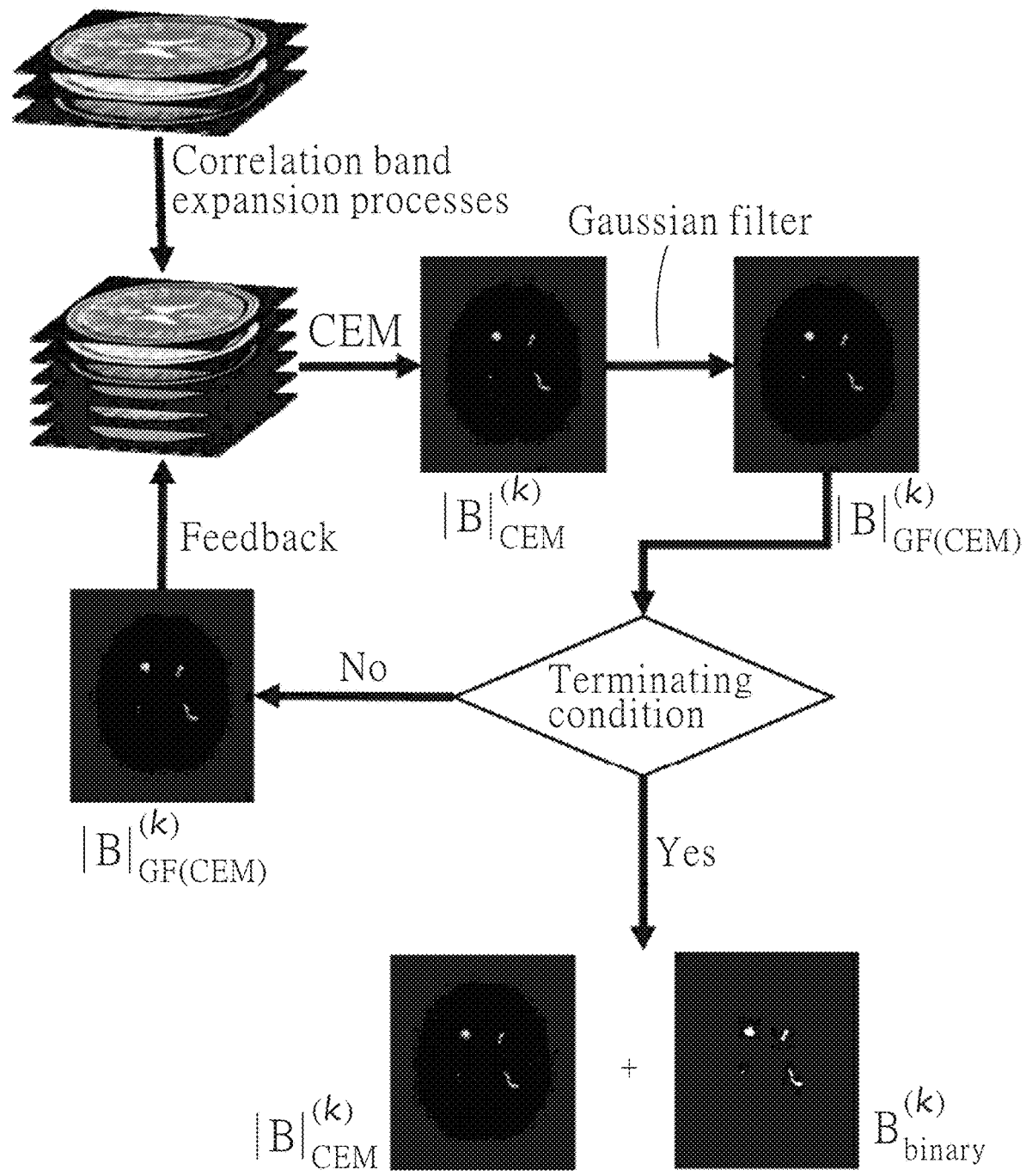
FIG. 3 shows a graphic flow chart of the embodiment of the present invention.
Figure 5A:
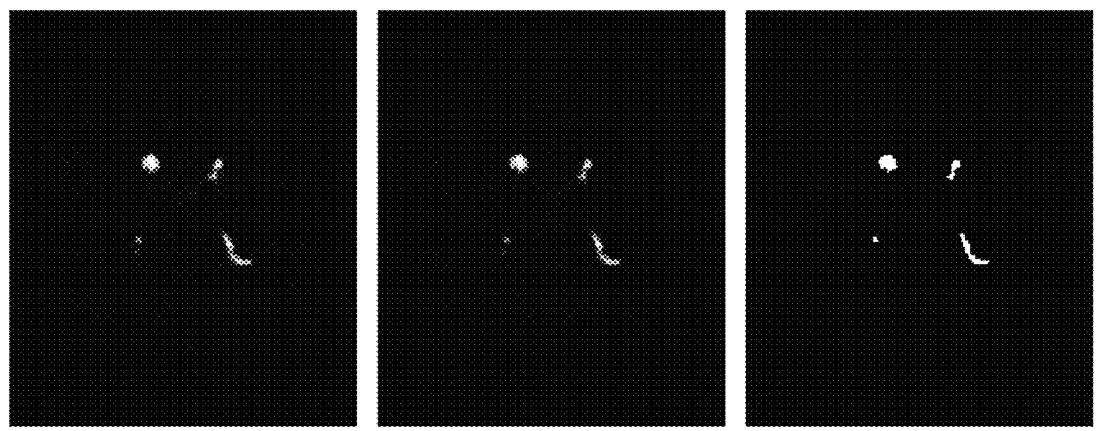
FIG. 5A shows the lesion detection result of the MRI image of noise and 0% INU by the iterative analyzing method for a medical image of the present invention, using the Gaussian window size of 3×3 specified by σ=0.1.
Figure 5B:
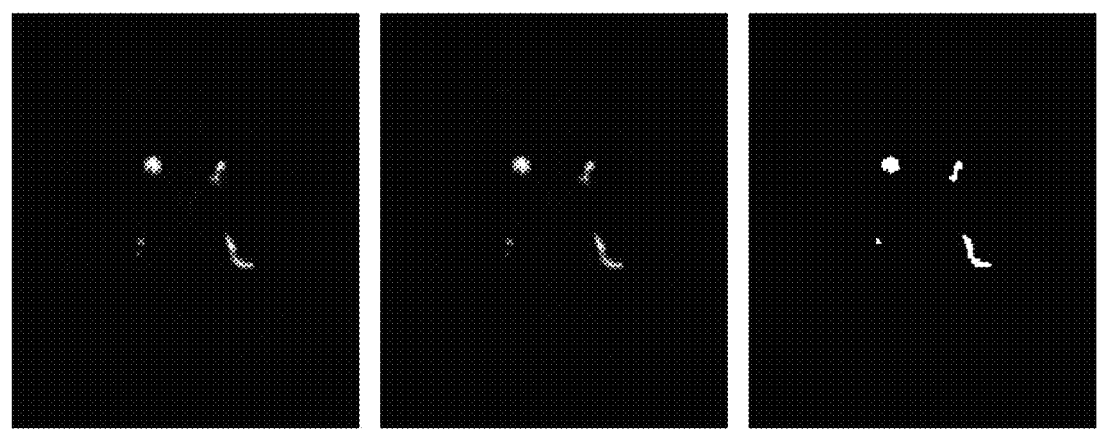
FIG. 5B shows the lesion detection result of the MRI image of noise and 0% INU by the iterative analyzing method for a medical image of the present invention, using the Gaussian window size of 5×5 specified by σ=0.5.
Figure 5C:
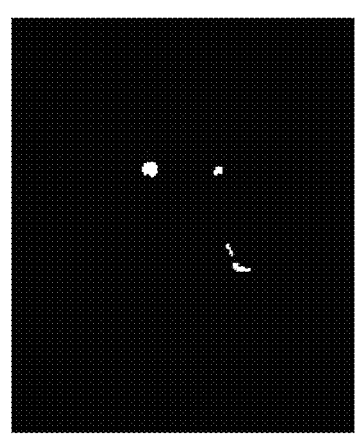
FIG. 5C shows the lesion detection result by the lesion segmentation tool, wherein the MRI image of noise and 0% INU.
Figure 6A:
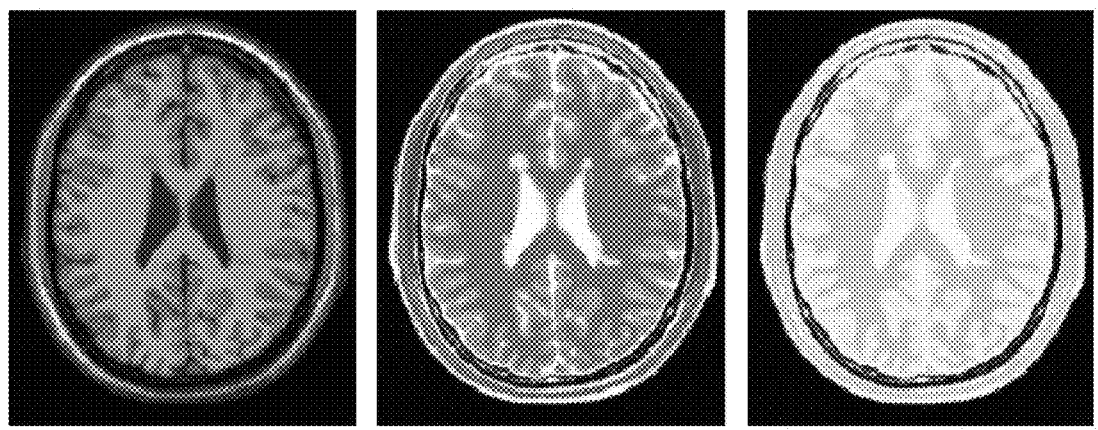
FIG. 6A shows the original slice of MS MR brain images with 1% noise and 0% INU acquired by T1, T2 and PD.
Figure 6B:
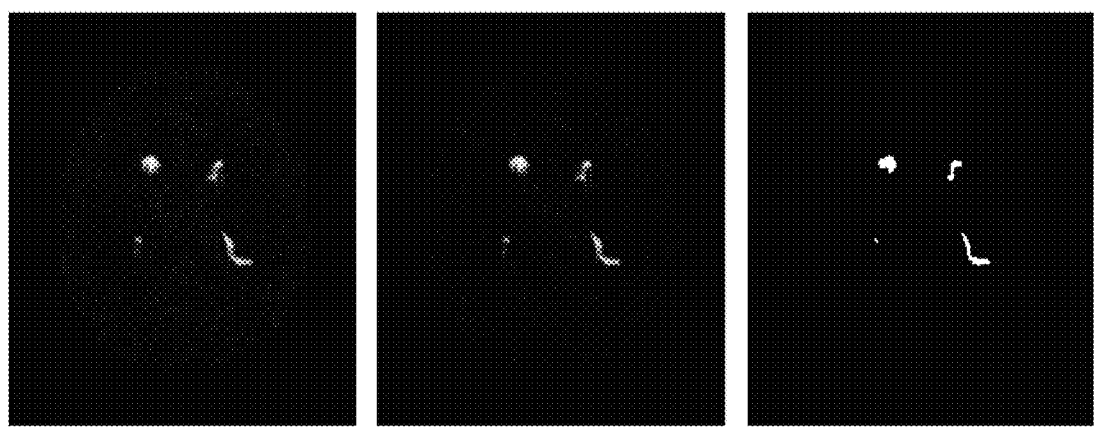
FIG. 6B shows the lesion detection result of the original slice of MS MR brain images in FIG. 6A by the iterative analyzing method for a medical image of the present invention, using the Gaussian window size of 3×3 specified by σ=0.1.
Figure 6C:
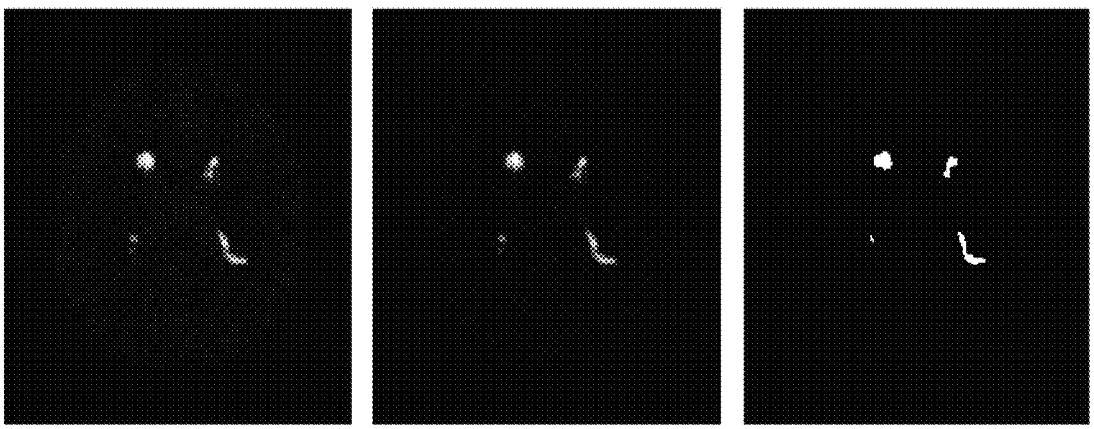
FIG. 6C shows the lesion detection result of the original slice of MS MR brain images in FIG. 6A by the iterative analyzing method for a medical image of the present invention, using the Gaussian window size of 5×5 specified by σ=0.5.
Figure 6D:
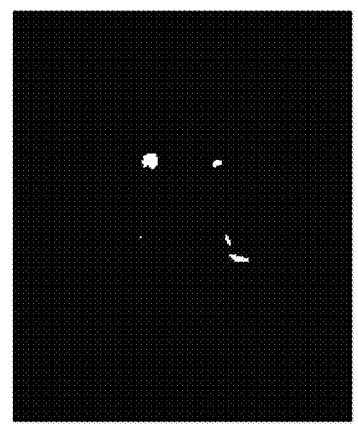
FIG. 6D shows the lesion detection result of the original slice of MS MR brain images in FIG. 6A by the lesion segmentation tool.
Figure 7A:
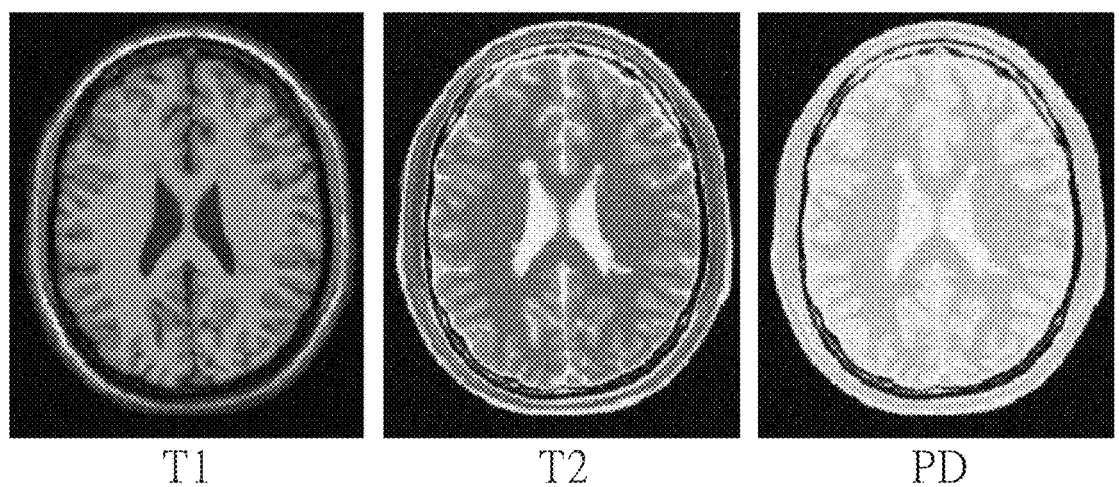
FIG. 7A shows the original slice of MS MR brain images with 3% noise and 0% INU acquired by T1, T2 and PD.
Figure 7B:
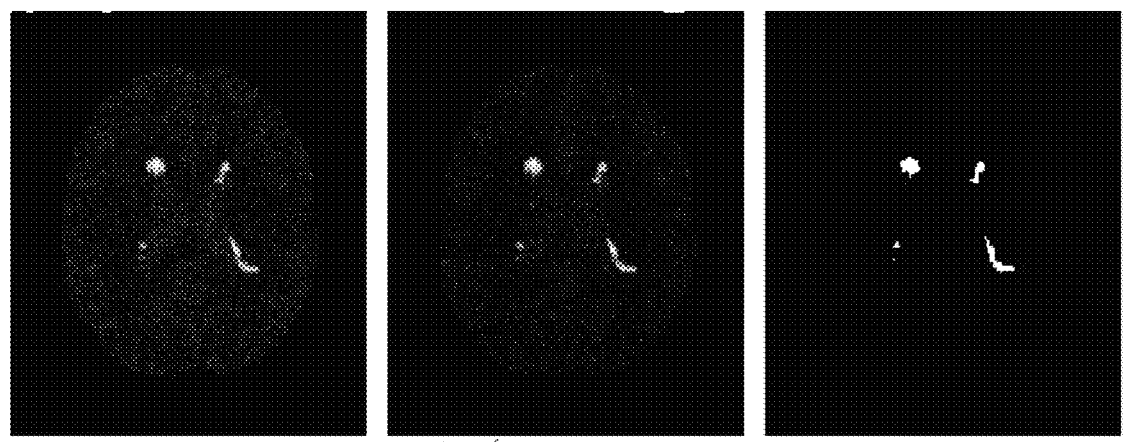
FIG. 7B shows the lesion detection result of the original slice of MS MR brain images in FIG. 7A by the iterative analyzing method for a medical image of the present invention, using the Gaussian window size of 3×3 specified by σ=0.1.
Figure 7C:
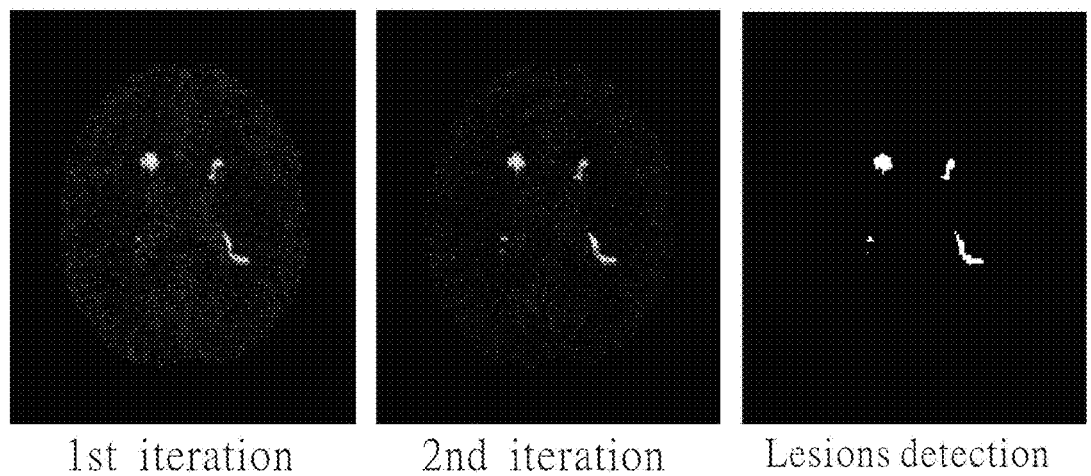
FIG. 7C shows the lesion detection result of the original slice of MS MR brain images in FIG. 7A by the iterative analyzing method for a medical image of the present invention, using the Gaussian window size of 5×5 specified by σ=0.5.
Figure 7D:
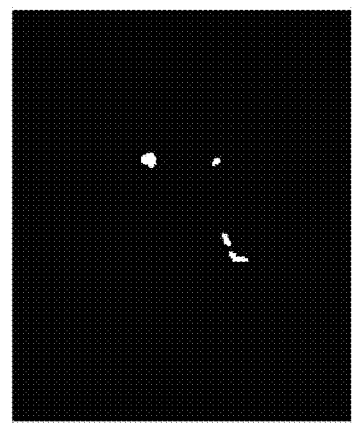
FIG. 7D shows the lesion detection result of the original slice of MS MR brain images in FIG. 7A by the lesion segmentation tool.
Figure 8A:
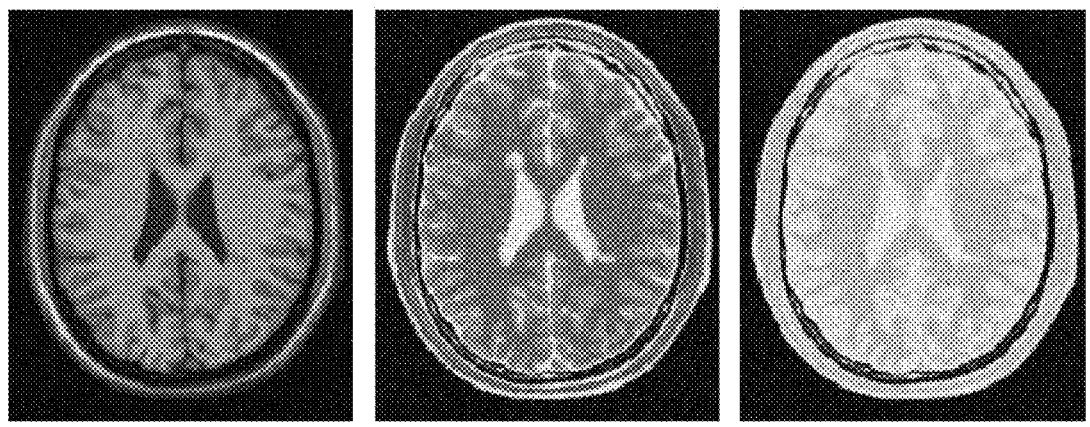
FIG. 8A shows the original slice of MS MR brain images with 5% noise and 0% INU acquired by T1, T2 and PD.
Figure 8B:
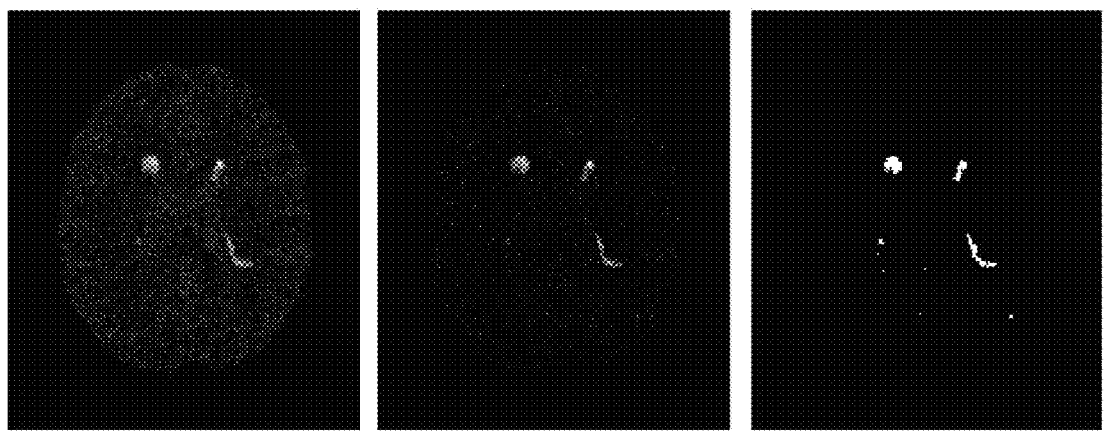
FIG. 8B shows the lesion detection result of the original slice of MS MR brain images in FIG. 8A by the iterative analyzing method for a medical image of the present invention, using the Gaussian window size of 3×3 specified by σ=0.1.
Figure 8C:
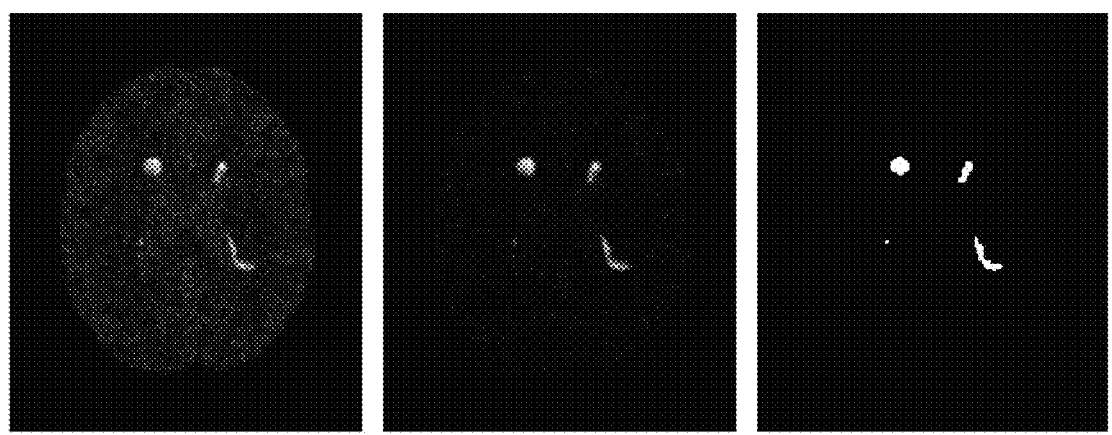
FIG. 8C shows the lesion detection result of the original slice of MS MR brain images in FIG. 8A by the iterative analyzing method for a medical image of the present invention, using the Gaussian window size of 5×5 specified by σ=0.5.
Figure 8D:
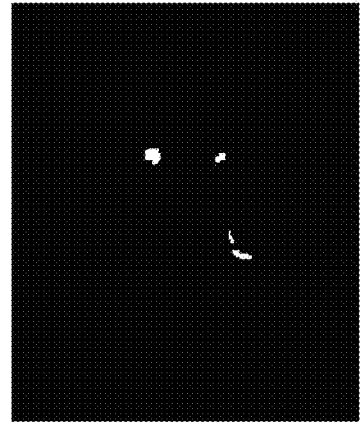
FIG. 8D shows the lesion detection result of the original slice of MS MR brain images in FIG. 8A by the lesion segmentation tool.
Figure 9A:
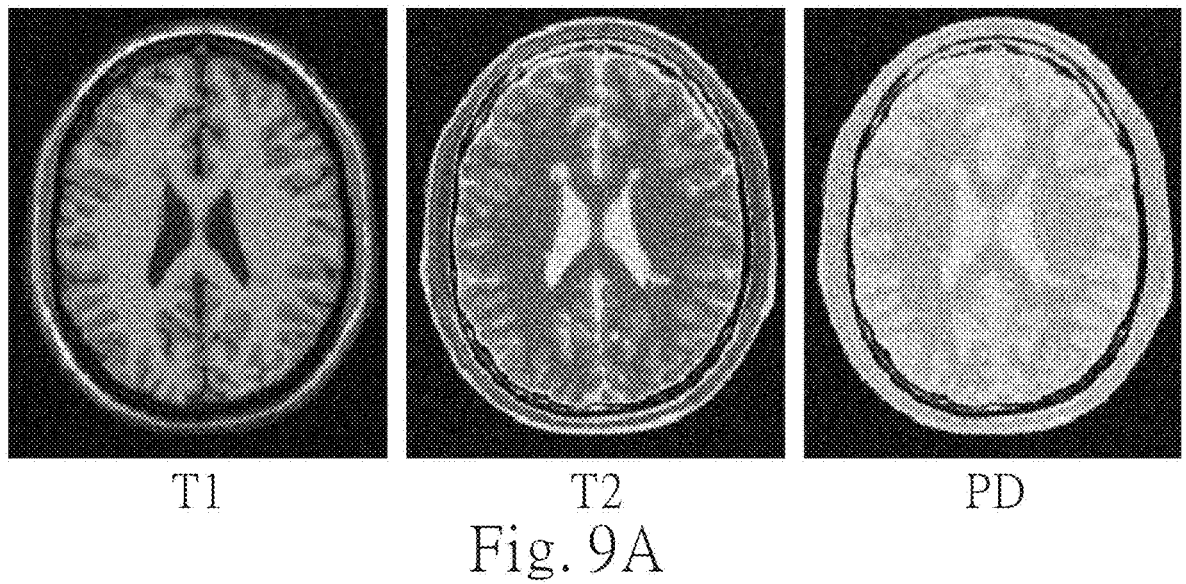
FIG. 9A shows the original slice of MS MR brain images with 7% noise and 0% INU acquired by T1, T2 and PD.
Figure 9B:
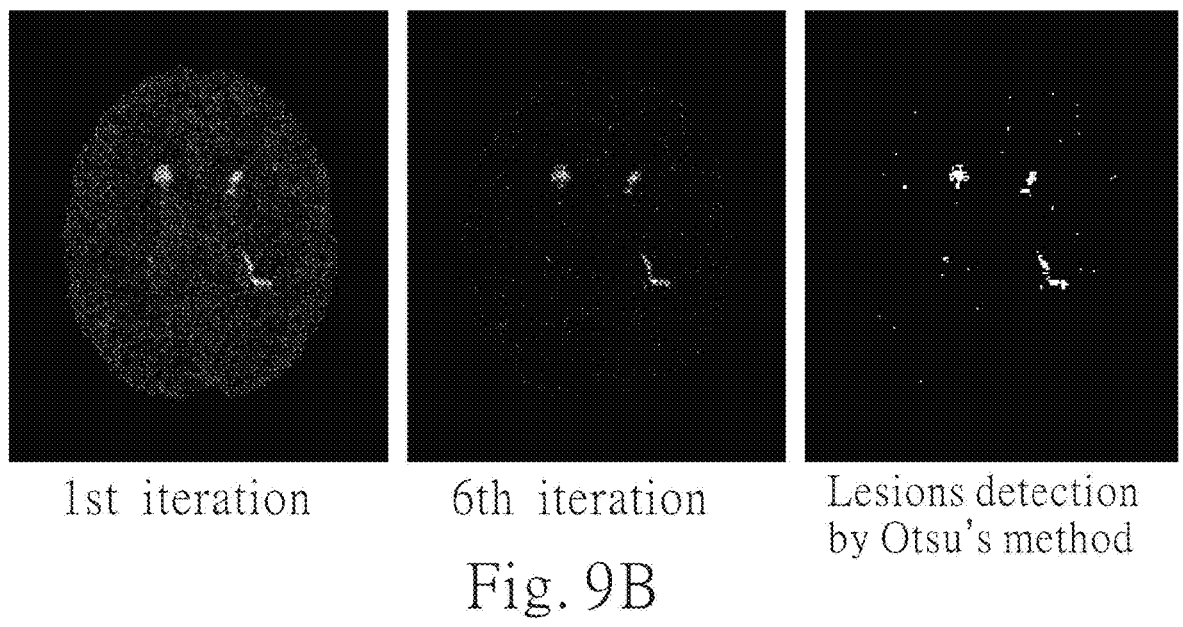
FIG. 9B shows the lesion detection result of the original slice of MS MR brain images in FIG. 9A by the iterative analyzing method for a medical image of the present invention, using the Gaussian window size of 3×3 specified by σ=0.1.
Figure 10A:
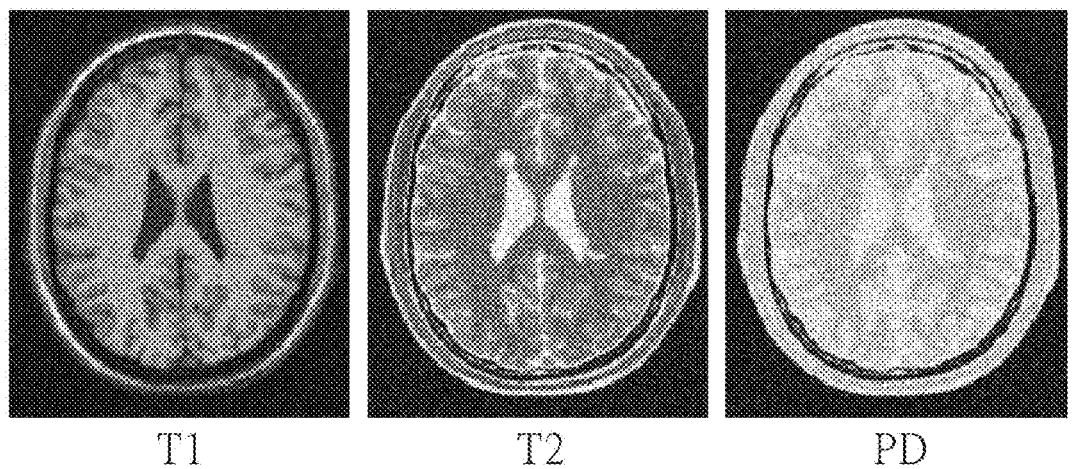
FIG. 10A shows the original slice of MS MR brain images with 9% noise and 0% INU acquired by T1, T2 and PD.
Figure 10B:
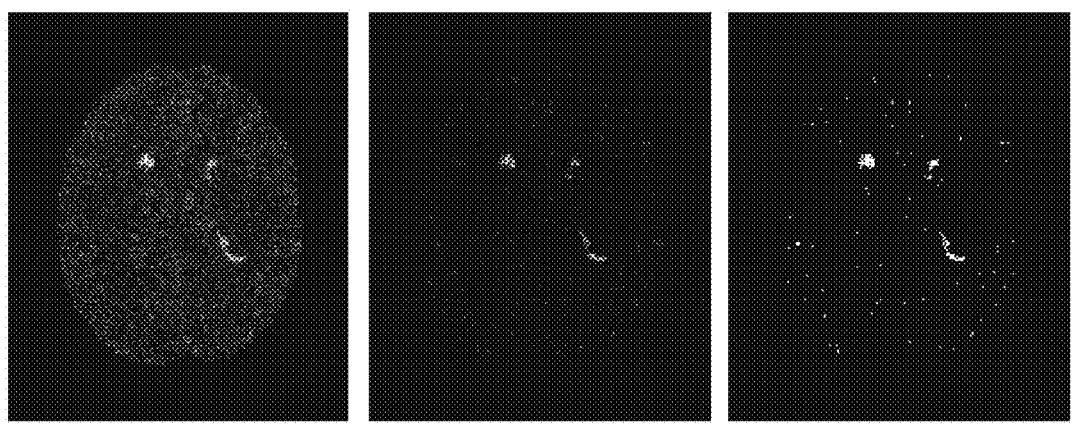
FIG. 10B shows the lesion detection result of the original slice of MS MR brain images in FIG. 10A by the iterative analyzing method for a medical image of the present invention, using the Gaussian window size of 3×3 specified by σ=0.1.
Figure 10C:
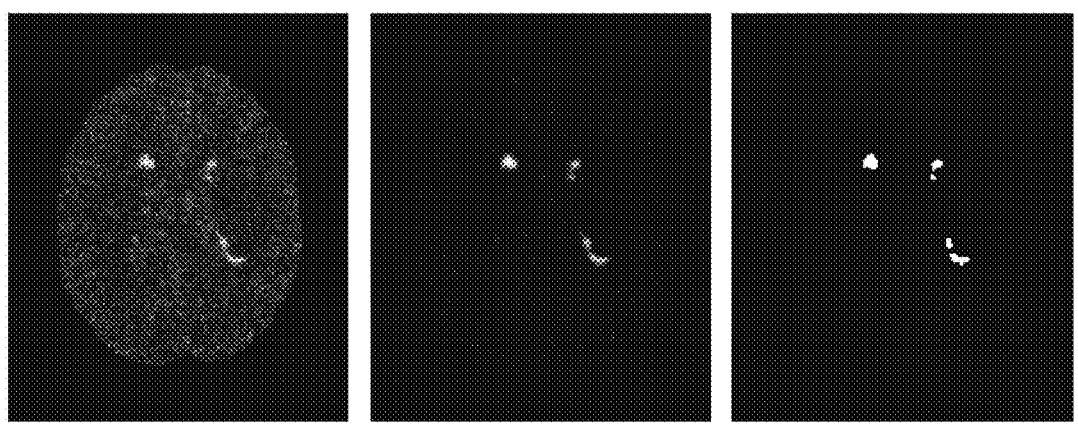
FIG. 10C shows the lesion detection result of the original slice of MS MR brain images in FIG. 10A by the iterative analyzing method for a medical image of the present invention, using the Gaussian window size of 5×5 specified by σ=0.5.

Furthermore, please refer to FIG. 1 to FIG. 3, one embodiment of the iterative analyzing method for a medical image disclosed by the present invention comprises the following steps:
101: Initial condition: Let $\{B_l\}_{l=1}^{L}$ be the original set of band images.
102: Using NBE process to create a set of nonlinear band images $\{B_i^{NB}\}_{i=1}^{n_{NB}}$ from the original set of band images, wherein $n_{NB}$ is the number of new band images by NBE process.
103: Collect the original set of band images and the set of nonlinear band images to produce a spectral image cube $\Omega(0)$ (the formula is $\Omega^{(0)}=\{B_l\}_{l=1}^{L} Y\{B_i^{NB}\}_{i=1}^{n_{NB}}$). Choose the desired target pixels d(0) from the spectral image cube $\Omega(0)$ and calculate autocorrelation R(0). The spectral image cube $\Omega(0)$ and calculate autocorrelation R(0) are required for constrained energy minimization.
104: At the $k^{th}$ iteration, update $d^{(k)}$ and $R^{(k)}=\sum_{i=1}^{N} r_i^{(k)}(r_i^{(k)})^T$ from $W^{(k)}$, wherein k is 1.
105: Use new generated $d^{(k)}$ and $R^{(k)}$ for $\delta_k^{CEM}$ to be implemented on $\Omega^{(k)}$. Let $B_{CEM}^{(k)}$ be the detection abundance fractional map produced by $\delta_k^{CEM}$.

106: Use a Gaussian filter to blur $|B|_{CEM}^{(k)}$, wherein $|B|_{CEM}^{(k)}$ is the absolute value of $B_{CEM}^{(k)}$. The resulting image is denoted by Gaussian-filter $|B|_{GFCEM}^{(k)}$.

107: Check if $|B|_k^{CEM}$ satisfies a predetermined termination condition. If no, continue step 108. Otherwise, go to step 109.

The predetermined termination condition is calculated by similarity index. In order to determine the predetermined termination condition, $S_k$ is obtained from the abundance image $|B|_{GF(CEM)}^{(k)}$ of $k^{th}$ iteration using Otsu's method to produce threshold, and then classify to obtain a binary image $B_{binary}^{(k)}$. $SI^k$ is calculated from $B_{binary}^{(k)}$ and the k-1$^{st}$ binary image $B_{binary}^{(k-1)}$.

The formula is below:

$$SI^{(k)} = \frac{2*|S_k \cap S_{k-1}|}{|S_k \cup S_{k-1}|}$$

Wherein $|S|$ is size of a set S, $S_k$ and $S_{k-1}$ are the $k^{th}$ thresholded binary image of the $k^{th}$ CEM detection abundance fractional map, $|B|_k^{CEM}$ and k-1$^{st}$ thresholded binary image of the k-1$^{st}$ CEM detection abundance fractional map, $|B|_{k-1}^{CEM}$.

108: Form spectral image cube $\Omega(K+1)$, which is the collection of spectral image cube $\Omega(K)$ and the spatial spectral image $|B|_{GF(CEM)}^{(k)}$ ($\Omega^{(k+1)}=\Omega^{(k)}Y\{|B|_{GFCEM}^{(k)}\}$). Let k←k+1 and go to step 4.

109: Produce the abundance image $B_{CEM}^{(k)}$ and is the spatial spectral image $|B|_{GF(CEM)}^{(k)}$.

According to the iterative analyzing method for a medical image of the present invention, when it processing the $i^{th}$ iteration, the abundance image will be obtained and then take an absolute value of the abundance image $B_{CEM}^{(i)}$ for blurring by the Gaussian filter to produce a spatial spectral image $|B|_{GF(CEM)}^{(i)}$. The spatial spectral image is fed back to the original spectral image cube $\Omega_{NBEP}^{(i)}$ for producing another spectral image cube by collection and then process next iteration until the predetermined termination condition is satisfied. In other words, when it satisfies the predetermined termination condition, it will output the image result for accuracy judging the lesion.

In the following disclosure, specific details and figures are given to provide a thorough understanding of the embodiments of the present invention.

EXAMPLE 1

Analyzing the Simulation Sample

MR brain images containing multiple sclerosis (MS) lesions were obtained from the MR imaging simulator of McGill University, Montreal, Canada for experiments. MS lesions are typically hyperintense on T2 or FLAIR sequence image. FIG. 4a to FIG. 4C shows a slice MR brain image along with the ground truth of MS lesion shown in FIG. 4D. The MR brain images are acquired by the modalities of T1, T2 and PD with specifications provided in BrainWeb site. The thickness of slice is 1 mm with size of 181×217×181 (pixel). Each slice is specified by INU 0% or 20%, denoted by rf0 and rf20 with 6 different levels of noise, 0%, 1%, 3%, 5%, 7% and 9%. The noise in the background of the simulated images is simulated by Rayleigh statistics and signal regions are simulated by Rician statistics, wherein the "percentage (%) of noise" represents the ratio of the standard deviation of the white Gaussian noise to the signal for a reference tissue in terms of %.

The selected 23 MR images were analyzed by the iterative analyzing method for a medical image of the present invention. Table 1 specifies the values of parameters used for this example, wherein n represents noise and its following number represents the level of noise; rf represents non-uniformity and its following number represents the non-uniformity ratio; the number before the parentheses represents the number of iterations when the window size is 3×3; and the number in the parentheses represents the number of iterations when the window size is 5×5

TABLE 1

The parameters used for BrainWeb images

| Band images | T1、T2、PD (3 bands) | | | | | |
|---|---|---|---|---|---|---|
| Correlation Band Expansion Process (CBEP) d | 3$^{rd}$ order correlated band images | | | | | |
| Iteration # | Manual selection | | | | | |
| | n0rf0 | n1rf0 | n3rf0 | n5rf0 | n7rf0 | n9rf0 |
| | 2 (2) | 2 (2) | 2 (2) | 4 (2) | 6 (3) | 7 (4) |
| | n0rf20 | n1rf20 | n3rf20 | n5rf20 | n7rf20 | n9rf20 |
| | 2 (2) | 2 (2) | 2 (2) | 3 (3) | 5 (3) | 6 (3) |
| Gaussian window size | 3 × 3 or 3 × 3 | | | | | |
| σ used in Gaussian filter | 0.1 with window size 3 × 3 (0.5 with window size3 × 3) | | | | | |
| Thresholding method | Otsu's method | | | | | |
| error threshold (DSI, Dice similarity index) | 0.80 | | | | | |

Each of the selected 23 MR images is analyzed by the iterative analyzing method for a medical image of the present invention with the parameters shown in Table 1 and also analyzed by the Lesion segmentation tool (called LST). The results shown in FIG. 5 to FIG. 10, wherein the first parameter represents 3×3 of mask size and σ of 0.1 and the second parameter represents 5×5 of mask size and σ of 0.5. Moreover, the DSI value from the different analysis method are averaged over 23 MR images, as shown in Table 2.

TABLE 2

Averaged DSI values of lesions detection by the method of the present invention and LST

| | Methods | | |
|---|---|---|---|
| Noise INU level | The method of the present invention with the first parameter | The method of the present invention with the second parameter | LST |
| n0rf0 | 0.865 | 0.808 | 0.739 |
| n1rf0 | 0.886 | 0.864 | 0.749 |
| n3rf0 | 0.893 | 0.863 | 0.750 |
| n5rf0 | 0.806 | 0.839 | 0.731 |
| n7rf0 | 0.652 | 0.822 | 0.693 |
| n9rf0 | 0.579 | 0.801 | 0.714 |
| n0rf20 | 0.861 | 0.829 | 0.733 |
| n1rf20 | 0.867 | 0.834 | 0.753 |
| n3rf20 | 0.881 | 0.827 | 0.746 |
| n5rf20 | 0.814 | 0.831 | 0.732 |
| n7rf20 | 0.714 | 0.825 | 0.694 |
| n9rf20 | 0.540 | 0.806 | 0.655 |

According to Table 1, it shows that when the noise is below 3%, the number of iteration is 2, and when the noise is over 5%, the number of iteration is over 2, the number of iteration with the window (mask) size of 3×3 is more than that with the window (mask) size of 5×5. Furthermore, when the window (mask) size is small and the level of noise increases, the number of iteration will increase more; and the window (mask) size is large and the level of noise increases, the number of iteration will increase less. In other words, the iterative analyzing method for a medical image of the present invention needs more number of iteration when the noise is higher.

Moreover, the DSI value is over 0.8 by the iterative analyzing method for a medical image of the present invention, but the DSI value is only 0.655~0.753 by LST. Compared DSI value detected by the method of present invention and LST, it shows that the iterative analyzing method for a medical image of the present invention has better accuracy of lesion detection in the images.

Additionally, according to Tables 1 and 2, when the noise level is low (0%, 1%, 3%), the method of the present invention performed better whether the size of Gaussian window is. And when the noise level is high (5%, 7%, 9%). It performed better by using a smaller Gaussian window.

EXAMPLE 2

Analyzing the Real Sample

The real MRI brain images were acquired at the Taichung Veterans General Hospital (TCVGH) by Siemens Magnetom Aera 1.5 Tesla MR scanner with a 16-channel phase-array head coil. MR imaging protocol included T1 with 3D MPRAGE, T2 and FLAIR with SPACE technique. Other imaging parameters used for data acquisition were voxel size of 1×1×1 mm, matrix size of 256×256×176, and NEX=1. The protocol for this study was approved by the Ethics Committee of Clinical Research, TCVGH (IRB number: CE16138A). According to a clinical visual inspection criterion, called white matter hyperintensities (WMH), the WMH lesions can be graded by Fazekas with three grades of Fazekas shown in FIG. 11 for illustration.

The real MRI brain images were analyzed by the iterative analyzing method for a medical image of the present invention and LST, respectively, wherein the parameters used for the method of the present invention were shown in Table 3. The analysis results were shown as FIG. 12 to FIG. 14.

TABLE 3 the parameters used for the method of the present invention

| Band | T1、T2、FLAIR (3 bands) | | |
|---|---|---|---|
| CBEP | 3rd order correlated band images | | |
| d | Manual selection | | |
| Fazekas grade | 1 | 2 | 3 |
| Iteration # | 2 | 2 | 2 |
| Gaussian window size | 5 × 5 | | |
| $\sigma$ used in Gaussian filter | 0.5 with window size 5 × 5 | | |
| Thresholding method | Otsu's method | | |
| stopping threshold (DSI) | 0.80 | | |

Figure 14B:
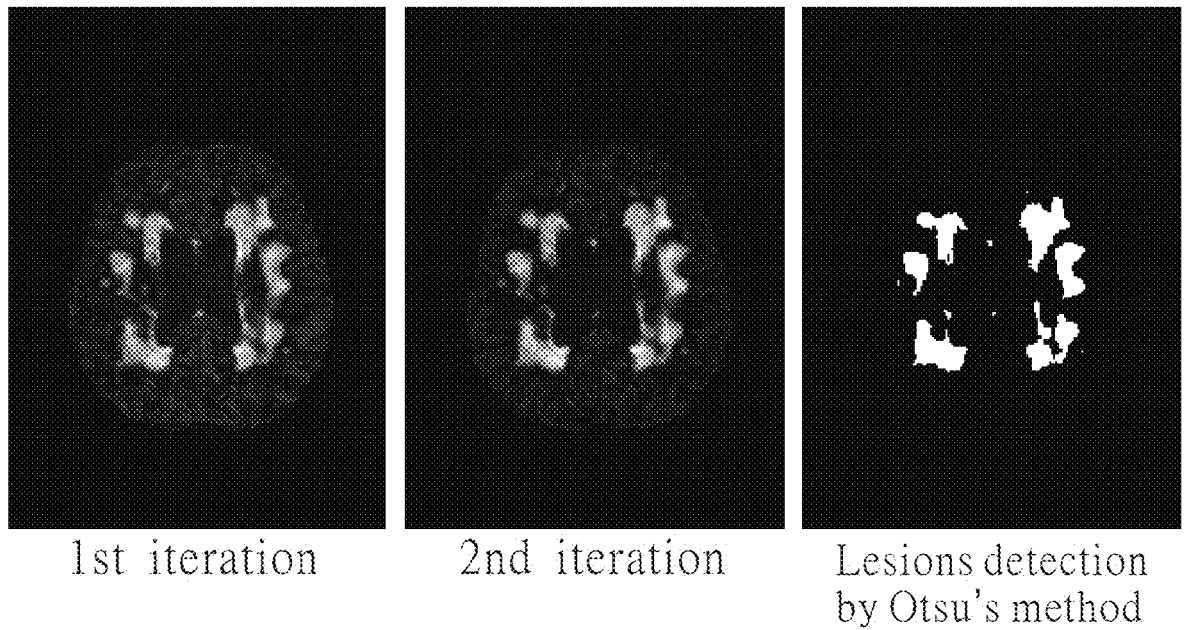
FIG. 14B shows the lesion detection result of the original slice of MS MR brain images in FIG. 14A by the iterative analyzing method for a medical image of the present invention, using the Gaussian window size of 5×5 specified by σ=0.5.
Figures 14C, 14D:
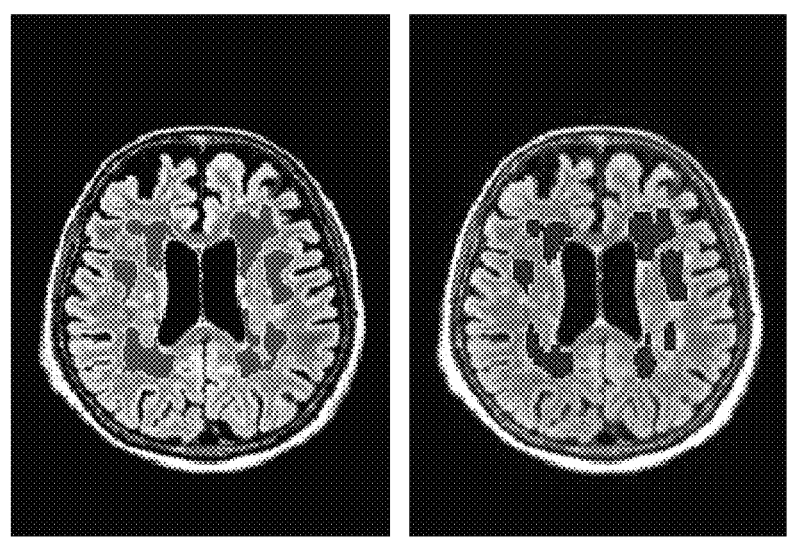
FIG. 14C shows the lesion detection result of the original slice of MS MR brain images in FIG. 14A by the iterative analyzing method for a medical image of the present invention.
FIG. 14D shows the lesion detection result of the original slice of MS MR brain images in FIG. 14A by the lesion segmentation tool.

According to FIGS. 12 to 14, the number of iterations carried out by the method of the present invention is always two for all three Fazekas grades. As also demonstrated in example 1, the number of iterations required by the method of the present invention was affected by noise levels not WMH grades by Fazekas.

Secondly, the method of the present invention can detect the lesion area accurately by obtaining the spatial information, especially for the edge and boundary pixels. Please see FIG. 13 and FIG. 14, it shown that the lesion area detected by LST is obviously smaller than that detected by the method of the present invention. That is, the accuracy of the present invention is much better than LST.

What is claimed is:

1. An iterative analyzing method for a medical image, comprising the following steps:
   (a) obtaining a $N^{th}$ spectral image cube, wherein N is a positive integer;
   (b) detecting a relative matrix and a desired target sub-pixel from the $N^{th}$ spectral image cube to produce a $N^{th}$ abundance image;
   (c) obtaining an absolute value of the $N^{th}$ abundance image for blurring and then producing a $N^{th}$ spatial spectral image;
   (d) analyzing the $N^{th}$ spatial spectral image to produce a $N^{th}$ threshold and transferring the $N^{th}$ abundance image to a $N^{th}$ binary image by the $N^{th}$ threshold; and
   (e) calculating a $N^{th}$ similarity index by the $N^{th}$ threshold and the $N-1^{st}$ threshold, wherein:
   if the $N^{th}$ similarity index satisfies a predetermined termination condition, the analyzing result includes the $N^{th}$ binary image and the $N^{th}$ spatial spectral image, or the $N^{th}$ similarity index does not satisfy the predetermined termination condition, it makes N of steps b to e to N+1 and collects the $N^{th}$ spectral image cube and the $N^{th}$ spatial spectral image to obtain a $N+1^{st}$ spectral image cube for repeating steps b to e.

2. The iterative analyzing method of claim 1, wherein when N is 1, the $N^{th}$ set of band images are dimensional-expanded from at least one original band image by a nonlinear method.

3. The iterative analyzing method of claim 2, wherein the original band image is imaged by different wave signals.

4. The iterative analyzing method of claim 3, wherein the original band image is MRI image, computed tomography image, or optical image.

5. The iterative analyzing method of claim 1, wherein, in the step b, the method for detection is constrained energy minimization.

6. The iterative analyzing method of claim 1, wherein, in the step c, it uses a smoothing filter to blur the absolute value of the $N^{th}$ abundance image.

7. The iterative analyzing method of claim 6, wherein when the noise of the image is higher, the mask size of the smoothing filter is bigger.

8. The iterative analyzing method of claim 1, wherein the $N^{th}$ threshold is used for distinguishing the image foreground grayscale value from the image background grayscale value.

9. The iterative analyzing method of claim 1, wherein the predetermined termination condition is the $N^{th}$ similarity index less than 0.7~0.9.

10. The iterative analyzing method of claim 9, wherein the predetermined termination condition is the $N^{th}$ similarity index less than 0.8.

* * * * *